United States Patent [19]

Igari et al.

[11] Patent Number: 5,344,644
[45] Date of Patent: Sep. 6, 1994

[54] WATER-SOLUBLE COMPOSITION FOR SUSTAINED-RELEASE

[75] Inventors: Yasutaka Igari, Kobe; Minoru Yamada; Seiko Ishiguro, both of Kawanishi, all of Japan

[73] Assignee: Takeda Chemical Industries, Ltd., Osaka, Japan

[21] Appl. No.: 919,401

[22] Filed: Jul. 23, 1992

[30] Foreign Application Priority Data

Aug. 1, 1991 [JP] Japan .................................. 3-192874

[51] Int. Cl.⁵ .............................................. A61K 45/05
[52] U.S. Cl. .................................... 424/85.1; 424/85.2; 424/85.4; 514/2; 514/12; 514/21
[58] Field of Search ...................... 424/85.1, 85.2, 85.4; 514/2, 12, 21

[56] References Cited

U.S. PATENT DOCUMENTS

| | | | |
|---|---|---|---|
| 4,447,355 | 5/1984 | Sakamoto et al. | 424/85.2 |
| 4,585,754 | 4/1986 | Meisner et al. | 514/8 |
| 4,609,640 | 9/1986 | Morashita et al. | 514/12 |
| 4,857,505 | 8/1989 | Arendt | 514/12 |
| 5,013,714 | 5/1991 | Lindstrom et al. | 514/12 |
| 5,024,841 | 6/1991 | Chu et al. | 424/85.4 |

FOREIGN PATENT DOCUMENTS

| | | |
|---|---|---|
| 0123291 | 4/1984 | European Pat. Off. ...... A61K 45/02 |
| 0312208 | 4/1989 | European Pat. Off. . |
| 0307097 | 9/1989 | European Pat. Off. . |
| 6143632 | 2/1988 | Japan . |
| 0126634 | 2/1990 | Japan . |
| 9200745 | 1/1992 | World Int. Prop. O. . |

OTHER PUBLICATIONS

Ramsden, et al., "Selective & differential binding ... " Eur. J. Immunol., vol. 22, pp. 3027–3031, 1992.
D. M. Sylvester et al., "Augmentation of Antimetastatic Activity of Interferon and Tumor Necrosis Factor by Heparin"; Immunopharmacology and Immunotoxicology 12(2), 161–180 (1990).
D. E. Ingber et al., "A Possible Mechanism for Inhibition of Angiogenesis by Angiostatic Steriods: Induction of Capillary Basement Membrane Dissolution" Endo. 1986, vol. 119, No. 4, pp. 1768–1775.
D. Gospodarowicz et al.; "Heparin Protects Basis and Acidic FGF from Inactivation", Journal of Cellular Physiology 128:475–484 (1986).

*Primary Examiner*—Michael G. Wityshyn
*Assistant Examiner*—C. Sayala
*Attorney, Agent, or Firm*—David G. Conlin; George W. Neuner

[57] ABSTRACT

A water soluble composition is described which comprises (a) a water soluble pharmacologically active peptide selected from the group consisting of cytokines or haematopoietic factors and (b) a sulfate group-containing acidic mucopolysaccharide and/or a desulfated modification of a naturally occurring sulfate group containing acidic mucopolysaccharide, and which brings about prolonged action of pharmacologically active peptides in a living body.

5 Claims, 3 Drawing Sheets

WATER-SOLUBLE COMPOSITION FOR SUSTAINED-RELEASE

FIELD OF THE INVENTION

The present invention relates to a water-soluble composition useful as a sustained-release, or prolonged-action, preparation of a pharmacologically active and water-soluble peptide.

BACKGROUND OF THE INVENTION

Long-acting preparations containing pharmacologically active substances, in particular peptide drugs, are used to maintain the body fluid concentration of each peptide within a certain effective concentration range over a prolonged period of time. Such substances include, according to the mechanisms of manifestation of their pharmacological effects,
   a) pharmacologically active substances whose pharmacological effects do not much depend on their effective body fluid concentrations and will not be harmful to living bodies even when manifested excessively, and
   b) pharmacologically active substances whose pharmacological effects depend on their effective body fluid concentrations and may be harmful to living bodies when manifested abruptly or excessively, so that dose adjustment is required at regular intervals.

Japanese Patent Application Laid-open No. 213/1990 discloses a technology of long-acting preparations of physiologically active peptides which contain hyaluronic acid and nontoxic salts thereof. In an example, a long-acting calcitonin or elcatonin preparation containing sodium hyaluronate in a concentration of 5% was subcutaneously administered to male rats. Reduction in blood calcium level lasted at least 12 hours. Similarly, when a long-acting human growth hormone preparation containing sodium hyaluronate in a concentration of 5% was administered to male rats, a blood human growth hormone concentration was found lasting at least 12 hours. With these preparations, an obvious prolongation of the residence in blood was observed as compared with a comparative example in which sodium hyaluronate was not used. However, in another comparative example in which a tegafur preparation containing sodium hyaluronate in a concentration of 5% was subcutaneously administered to male rats, no prolonging effect was observed.

These inventions utilize the retarded diffusion, at the site of administration, of a substance in solution as caused by the viscosity of hyaluronic acid. However, cationic group-containing substances may undergo ion exchange with carboxyl-containing hyaluronic acid macromolecules and this exchange can further retard the diffusion of said substances. Japanese Patent Application Laid-open No. 213/1990 mentions 3 to 7% as the most preferred concentration of hyaluronic acid itself. However, because of its high viscosity, bubbles may be formed and, if formed, pose a great problem, namely, centrifugation or deaeration under reduced pressure is required for the elimination thereof. At the same time, its high viscosity makes it necessary to use a large-gauge injection needle, and the pain possibly caused thereby cannot be ignored.

Japanese Patent Application Laid-open No. 287041/1989 describes an example in which hyaluronic acid is used in a concentration of 1%. The "caution in use" for a preparation sold on the mark, an intraarticular injection containing sodium hyaluronate in the same concentration of 1%, recommends the use of a fairly large-gauge needle of about 18–20 G. Such preparation, as an injection for subcutaneous administration, can cause great pain in patients.

Furthermore, Japanese Patent Application Laid-open No. 129226/1987 describes that the hyaluronic acid concentration in injectable products may range from about 0.05% to 4% (by weight) and may be higher depending on the final use of the products, without mentioning on any particular application to injections. At any rate, it is readily presumable by analogy that a retention prolonging effect on pharmacologically active substances cannot be obtained without using hyaluronic acid in a relatively high concentration, as mentioned above. There is a possibility that sustained release of pharmacologically active substances may be attained depending on the viscosity of a high concentration of hyaluronic acid. There is also a possibility that sustained release of pharmacologically active substances may be accomplished using the fact that the viscosity of hyaluronic acid can be increased by reducing the pH into the acid side (e.g. to about 2.5). However, a higher hyaluronic acid viscosity means a greater difficulty in the administration as an injection. In addition, there is a fear that a deviation of the pH of the hyaluronic acid solution from the physiological pH range may affect the stability of the pharmacologically active substances and/or cause damages to living body tissues at the site of administration.

In EP312208, it is disclosed that the combination of glycosaminoglycans such as hyaluronic acid, chondroitin, chondroitin-6-sulfate, chondroitin-4-sulfate, keratan sulfate, heparan sulfate, heparin and mitogenic or angiogenic polypeptide, growth factors such as epidermal growth factor (EGF), transforming growth factor (TGF), fibroblast growth factor (FGF), insulin like growth factor (IGF), platelet derived growth factor (PDGF) provides a good aqueous gel formulation for wound healing. But, there is no working example of the combination of glycosaminoglycan except hyaluronic acid and the polypeptide growth factors.

In WO91/00739, the technique to stabilize motilin by combining the peptide with heparin is described.

As mentioned above, several problems remain to be solved as regards the adaptability and compatibility in the administration to living bodies although attempts have been made to use hyaluronic acid in producing sustained release preparations of pharmacologically active substances.

SUMMARY OF THE INVENTION

The present inventors made intensive investigations in an attempt to solve the above problems and, as a result, found that water-soluble compositions comprising a water-soluble, pharmacologically active peptide in combination with a sulfate group-containing acidic mucopolysaccharide and/or a desulfated modification thereof can produce prolonged pharmacological effects without adversely affecting the pharmacological activities of the pharmacologically active, water-soluble peptide. As a result of further investigations based on this finding, they have completed the present invention.

The invention provides a water-soluble composition which comprises (a) a water soluble pharmacologically active peptide selected from the group consisting of cytokines, haematopoietic factors, peptide hormones, the factors that affect cardiovascular system, cell attachment factors, the factors that affect central and peripheral nerve system, the factors that affect body fluid electrolytes and organic blood constituents, the factors that affect bone and skeletal system, the factors that affect nephro-urinary system, the factors that affect sensory organs, the factors that affect immune system, the factors that affect respiratory system, the factors that affect genital system and enzymes and (b) a sulfate group-containing acidic mucopolysaccharide and/or a desulfated modification of a naturally occurring sulfate group-containing acidic mucopolysaccharide.

DETAILED DESCRIPTION OF THE INVENTION

Hereinafter, the above mentioned water soluble pharmacologically active peptide will be sometimes referred to as "pharmacologically active peptide" for short.

Hereinafter, the above mentioned sulfate group-containing acidic mucopolysaccharide and/or desulfated modification of naturally occurring, sulfate group-containing, acidic mucopolysaccharide will be sometimes referred to as "mucopolysaccharide of the invention" for short.

In the present invention, as said water soluble pharmacologically active peptide, one whose partition coefficient measured in octanol over water is below 0.1 is preferred, and one whose partition coefficient measured in octanol over water is below 0.05 is more preferred.

As said pharmacologically active peptide, one having molecular weight of about 200 to 200000 is preferred, and one having molecular weight of 300 to 90000 is more preferred.

As said pharmacologically active peptide, cytokines, haematopoietic factors, peptide hormones, the factors that affect central and-peripheral nerve system, the factors that affect bone and skeletal system, the factors that affect immune system, and the factors that affect genital system are preferred. As said pharmacologically active peptide, cytokines, haematopoietic factors and peptide hormone are more preferred.

As cytokines, lymphokines and monokines are listed. The lymphokines include interferons (e.g. alpha, beta, gamma) and interleukins (e.g. IL-2 to IL-11), and the monokines include IL-1, tumor necrotizing factor (e.g. TNF alfa and beta), and leukemic inhibitory factors (LIF).

Examples of haematopoietic factors include erythropoietin, granulocyte colony stimulating factors (G-CSF), granulocyte-macrophage colony stimulating factors (GM-CSF), macrophage colony stimulating factors (M-CSF).

Said haematopoietic factors also include ones that have thrombopoietic growth action, e.g., lymphocyte growth factor formulation (Leukoprol, Morinaga Milk, Japan), thrombopoietin, thrombocyte poiesis stimulatory factor, and megakaryocyte potentiator.

Examples of peptide hormones include insulin and growth hormone.

Examples of the factors that affect cardiovascular system include endothelin, endothelin synthetase inhibitor, endothelin antagonist, vasopressin, renin, angiotensin I, angiotensin II, angiotensin III, angiotensin I inhibitor, angiotensin II receptor antagonist, atrial natriuretic peptide (ANP), and antiarrhythmic peptide.

Examples of cell attachment factors include laminin and intercellular adhesion molecule 1 (ICAM 1).

Examples of the factors that affect central and peripheral nerve system include opioid peptides (e.g., enkephalin, endorphin, kyotorphin), neurotropic factor (NTF), calcitonin gene related peptide (CGRP), pituitary adenylate cyclase activating polypeptide (PACAP), thyrotropin releasing hormone (TRH) and salts and derivatives thereof (Japanese Patent Application Laid-open No. 121273/1975 and No. 116465/1977 corresponding to U.S. Pat. Nos. 3,959,247 and 4,100,152, respectively.), and neurotensin.

Examples of the factors that affect body fluid electrolytes and blood organic constituents include parathyroid hormone (PTH), calcitonin, apoprotein E, and hirudin.

Examples of the factors that affect bone and skeletal systems include bone Gla peptide, parathyroid hormone related peptide (PTH-rp) or its active fragment (osteostatin, Endocrinology, 129,324 (1991)) or histone H4-related osteogenic growth peptide (OGP) (The EMBO Journal, 11, 1867 (1992)) or muteins of any of them, or derivatives of any of them.

Examples of the factors that affect nephro-urinary system include those control the function of the kidney, e.g., brain natriuretic peptide and urotensin.

Examples of the factors that affect sensory organs include ones which control the sensitivity of the organs, e.g. substance P.

Examples of the factors that affect immune system include those that control inflammation and malignant neoplasm and that attacks infectire microorganisms, e.g. chemotactic peptide and bradykinin, and may further include natural derived, synthetic or genetically engineered peptides and proteins capable of serving as antigens, e.g., cedar pollen and ragweed pollen. These are administered alone, in a hapten-bound form, or together with an adjuvant in compositions of the present invention, in the form of injections.

Examples of the factors that affect respiratory system include those that control asthmatic reaction.

Examples of the factors that affect genital system include luteinizing hormone releasing hormone (LH-RH) or its analogue described in U.S. Pat. No. 4,008,209, oxytosin, and luteinizing hormone (LH).

Examples of enzymes include super oxide dismutase (SOD), tissue plasminogen activator (TPA) and kallikrein.

Said pharmacologically active peptide may further include soluble receptors for peptides.

Said pharmacologically active peptide may include those chemically modified with synthetic polymer such as polyethyleneglycol, natural polymers such as chondroitin, saccharides, or non-peptide substances. Said non-peptide substances may be either ligands for receptors or antigens for antibodies.

In addition, said pharmacologically active peptide may include naturally occurring one, chemically synthesized one and genetically engineered one.

In the context of the present invention, a pharmacologically active peptide may include a mutein being differing in sugar chain but having the activity, lacking in sugar chain, or different in partial amino acid sequence, a derivative, an analogue or a homologue of any of them which has the activity, or an active fragment of any of said peptide. The mode of action of pharmacologically active peptide may be anatagonisitic or agonistic.

The mucopolysaccharide used in the practice of the invention is preferably a long, linear, compound polysaccharide structurally composed of repetitions of a disaccharide unit comprising an aminosugar and a uronic acid. It may partially contain galactose in lieu of the uronic acid. It is a polyanion having a negative charge owing to the sulfate or carboxyl groups it contains.

Although the amino group of the anionic sugar residue of the mucopolypeptide is generally in an acetylated form, as the mucopolysaccharide one wherein a sulfate group is bound with the amino group in lieu of acetyl group may be included therein. Derivatives of these may also be used.

The mucopolysaccharide of the invention may be one derived from a biological tissue, such as cartilage, or one produced in a microorganism, or a derivative thereof. It has a molecular weight of, for example, 1,000 to 1,000,000, preferably about, 1,000 to 300,000, more preferably about 1,000 to 100,000.

The number of sulfate groups in the above-mentioned sulfate group-containing mucopolysaccharide is, for instance, about 0.01 to 4.0 per disaccharide unit, preferably about 0.1 to 3.0 per disaccharide unit.

As a method of desulfating nature-derived sulfate group-containing acidic mucopolysaccharides, there may be mentioned the method comprising carrying out desulfation using an acidic menthol solution (Schubert: Methods in Carbohydrate Chemistry, 5, 109 ff., 1965). The number of sulfate groups in the desulfated mucopolysaccharide of the invention is, for example, about 0 to 0.1, preferably about 0 to 0.05, per disaccharide unit.

As the sulfate group-containing mucopolysaccharide to be used in accordance with the invention, there may be mentioned, for example, chondroitin sulfate, keratan sulfate, heparin, and heparan sulfate. Among them, chondroitin sulfate, heparan sulfate and keratan sulfate are preferred.

The desulfated modification of the nature-derived, sulfate group-containing, acidic mucopolysaccharide, which is to be used in accordance with the invention, is, for example, chondroitin, desulfated heparin, or heparan. Chondroitin and heparan are preferred among others.

The mucopolysaccharide of the invention may be in the form of an alkali metal salt.

Said alkali metal salt is, for example, sodium salt or potassium salt. The sodium salt is preferred.

Said mucopolysaccharide may also be an alkaline earth metal salt, such as magnesium salt or calcium salt.

As regards the proportion of the pharmacologically active peptide in the composition, said peptide may be contained therein in an effective amount which may vary depending on the activity of said peptide and the therapeutic dose thereof. Generally, the weight ratio between the peptide and the mucopolysaccharide of the invention is preferably from about 0.00001:1 to about 10:1, more preferably about 0.0001:1 to about 5:1 or most preferably about 0.001:1 to about 1:1.

The composition of the invention may further contain a water-soluble protein injectable into body fluids without showing any substantial pharmacological activity at the concentration used in one unit dosage form of the present invention (hereinafter, "water-soluble protein" for short). As such water-soluble protein, there may be mentioned, among others, serum albumin, globulin, collagen and gelatin. Among them, serum albumin is preferred.

Although any particular mention cannot be made of the proportion of the water-soluble protein, either, said protein can be added in an amount generally employed in injectable pharmaceutical compositions. Thus, for example, the weight ratio between the water-soluble protein and the mucopolysaccharide is about 0.0001:1 to 100:1, preferably about 0,001:1 to about 10:1 or more preferably about 0.01:1 to about 1:1.

When the water-soluble composition of the invention is converted into an aqueous solution for administration, the concentration of the pharmacologically active peptide in said solution should preferably be about 0.0000001 to 10% (w/v), more preferably about 0.000001 to 5% (w/v) or most preferably about 0.00001 to 1% (w/v).

When said water-soluble composition is converted into an aqueous solution for administration, the concentration of the mucopolysaccharide in said solution should preferably be about 0.01 to 10% (w/v), more preferably about 0.1 to 5% (w/v) or most preferably about 0.1 to 2% (w/v).

When said water-soluble composition is converted into an aqueous solution, the concentration of the water-soluble protein in said solution should preferably be about 0.01 to 5% (w/v), more preferably about 0.01 to 1% (w/v) or most preferably about 0.01 to 0.5% (w/v).

The pH of a solution prepared from the water-soluble composition of the present invention should be such that said pH will not exert any adverse influence upon the activity of the pharmacologically active peptide but is within an acceptable range for injections in general and further such that said pH will neither cause a great change in viscosity of the solution nor allow formation of a precipitate or the like. Thus the solution should preferably have a pH of about 4 to 8, more preferably about 5 to 8.

The composition of the present invention should preferably have a unit dosage form containing the pharmacologically active peptide of the invention and the mucopolysaccharide of the invention, if necessary together with a water-soluble protein. Thus, for example, the two or three components mentioned above are made to occur in an ampule or vial by dissolving or suspending them in sterile water or sterile physiological saline. In this case, the method of preparation may comprise admixing a solution of the pharmacologically active peptide and a solution of the mucopolysaccharide and further, if necessary, a solution of a water-soluble protein, or adding the mucopolysaccharide and, if necessary, a water-soluble protein, each in a powder form, to a solution of the pharmacologically active peptide, or any other combination of adequate procedures. The dosage form may also be prepared by adding sterile water or sterile physiological saline to a lyophilizate or vacuum-dried powder in which the pharmacologically active peptide and the mucopolysaccharide and, if necessary, a water-soluble protein, coexist. This unit dosage form may further contain one or more of conventional additives such as pH adjusting agents (e.g. glycine, hydrochloric acid, sodium hydroxide), local anesthetics (e.g. xylocaine hydrochloride, chlorobutanol), isotonizing agents (e.g. sodium chloride, mannitol, sorbitol), and adsorption inhibitors (e.g. Tween 80).

This unit dosage form may further contain pharmaceutically acceptable excipients such as polyethylene glycol 400 or dextran.

The water-soluble composition of the present invention preferably takes the form of a parenteral preparation.

As said parenteral preparation, there may be mentioned injectable solutions, solutions for transmucosal administration, nasal solutions, otic solutions, etc.

Said injectable solutions include solutions for intravenous administration, for subcutaneous administration, for intraarterial administration, for intramuscular administration and for intraocular administration, among others. These long-acting preparations can be readily dragon from ampules or vials into syringes using a 25G or 26G needle, for instance. Bubbles, if formed upon the drawing, can be readily eliminated by a short time of mere standing.

The composition of the present invention may be in a form dissolved in water or in a lyophilized form with a crystalizing solute such as mannitol.

Addition of sterile water or sterile physiological saline to the lyophilizate gives an aqueous solution.

The tonicity of an aqueous solution of the water-soluble composition of the present invention should be within the tolerable range when administered and is adjusted, for example, by isotonizing agent such as sodium chloride and mannitol. The tonicity is preferably from half to twice as high as that of physiological saline, more preferably from three-quarters to one and a half as high as that of physiological saline.

The viscosity of an aqueous solution of the water-soluble composition of the present invention should be low enough to be injected. The viscosity is preferably lower than 500 cP, more preferably lower than 400 cP. The values of the viscosity corresponds to those measured by employing Cone LD in E type viscosity meter (TOKIMEC, Japan) at 25° C.

When the composition is in the form of a lyophilizate, it is required that the viscosity and the tonicity of and the component concentrations in the aqueous solution derived therefrom should be within the respective ranges mentioned hereinbefore.

The composition of the present invention is made by admixing these ingredients with a manner per se conventional method.

The goal of admixing the ingredients of the present composition should be such that the activity of the pharmacologically active substance is maintained and bubble formation minimized during the process. The ingredients are put into a vessel (for example bottle or drum) either at the same time or in any order. The atmosphere in the vessel can be, for example, sterile clean air or sterile clean nitrogen gas. The resultant solution can be transferred to small vials or ampules, and can be further subjected to lyophilization.

The liquid form or the lyophilizate powder form of the composition of the present invention may be dissolved or dispersed in a solution of biodegradable polymer such as poly(lactic-glycolic) acid copolymer, poly(hydroxybutyric acid), poly(hydroxybutyricglycolic) acid copolymer, or the mixture of these, and then may be formulated, for example, to films, microcapsules (microspheres), or nanocapsules (nanospheres) according to the well known methods.

In addition, the composition of the present invention encapsulated in liposomes comprising phospholipids, cholesterols or the derivatives of these according to the well known methods can be further dispersed in physiological saline or the hyaluronic acid solution dissolved in physiological saline.

A soft capsule may be filled with the liquid form of the composition of the present invention. A hard capsule may be filled with the lyophilizate powder of the composition of the present invention, or the lyophilizate powder of the present composition may be compressed to tablet for rectal administration or oral administration respectively. When hard capsule or tablet is administered, the effect of sustained-release is exhibited when it becomes a solution after administration.

Further, the composition of the present invention can be supplied in a prefilled syringe for self-administration, since the liquid formulation will not be subject to physical disturbances such as shaking due to its low viscous nature.

The composition of the present invention may be maintained at normal temperature such as from +10° C. to 30° C. or at normal refrigiration range, preferably from about +2° C. to +8° C.

The doses, target patients and target diseases of the composition of the present invention correspond to those of the pharmacologically active peptide. Mucopolysaccharide employed in the present invention is low toxicity.

Administration of a pharmacologically active peptide in admixture with an acidic mucopolysaccharide results in a prolonged residence of the pharmacologically active peptide in the living body, hence a prolonged manifestation of its pharmacological activity. The solutions of vary low viscosity of acidic mucopolysaccharides are capable of producing such effect, and therefore can be handled substantially in the same manner as ordinary solutions. As a result, small-gauge needles can be used for injection, and bubble formation or the like hardly occurs. The benefit to patients and medical personnel is immeasurable.

The following working examples and test examples are further illustrative of the present invention but are by no means limitative of the scope of the invention.

EXAMPLE 1

Physiological saline for injection (2 ml) was added to each vial of a human erythropoietin preparation (Epogin Injection 3000; Chugai Pharmaceutical, Japan) containing 3,000 international units (about 30 $\mu$g) of human erythropoietin, 25 mg of mannitol and 1 mg of human serum albumin to cause dissolution of the preparation. To 1.14 ml of the resultant solution was added 1.14 ml of a 1% chondroitin sulfate preparation (Kaken Pharmaceutical, Japan), followed by thorough mixing.

EXAMPLE 2

Physiological saline for injection (2 ml) was added to each vial of a human erythropoietin preparation (Epogin Injection 3000; Chugai Pharmaceutical) containing 3,000 international units (about 30 μg) of human erythropoietin, 25 mg of mannitol and 1 mg of human serum albumin to cause dissolution of the preparation. To 1.14 ml of the resultant solution was added 0.57 ml of a 1.5% (w/v) solution of chondroitin sodium salt (Seikagaku Corp., Japan) in physiological saline, followed by thorough mixing.

EXAMPLE 3

Physiological saline for injection (2 ml) was added to each vial of a human erythropoietin preparation (Epogin Injection 3000; Chugai Pharmaceutical) containing 3,000 international units (about 30 μg) of human erythropoietin, 25 mg of mannitol and 1 mg of human serum albumin to cause dissolution of the preparation. To 1.5 ml of the resultant solution were added 0.3 ml of physiological saline for injection and 10 mg of heparan sulfate sodium salt (Seikagaku Corp.), followed by thorough mixing.

EXAMPLE 4

Distilled water for injection (1 ml) was added to each vial of an interferon alfa preparation (Canferon A300; TAKEDA Chemical Industries, Japan) containing 3 million international units (about 100 μg) of interferon alfa-2a and 5 mg of human serum albumin to cause dissolution of the preparation. To 1.2 ml of the resultant solution was added 0.6 ml of a 1% chondroitin sulfate preparation (Kaken Pharmaceutical, Japan), followed by thorough mixing.

EXAMPLE 5

To 0.023 ml of granulocyte colony stimulating factor (G-CSF) preparation (Nupogen; Amgen, U.S.A.) containing 300 micrograms of G-CSF, 50 milligrams of mannitol, and 0.004% of Tween 80 were added 1.039 ml of physiological saline for injection (Fuso Pharmaceutical, Japan), 1.039 ml of a 1% chondroitin sulfate preparation (Kaken Pharmaceutical), and 4 microliters of Nichiyaku Albumin (Nihon Pharmaceutical, Japan) containing 20% (v/v) human serum albumin, followed by thorough mixing.

EXAMPLE 6

In 5 ml of 0.1N hydrochloric acid was added 10 mg of pig insulin (Diosynth; Netherland). A glass vial (capacity: ca. 5 ml) containing 1 ml of the above solution was added 1 ml of 1% chondroitin sulfate preparation (Kaken Pharmaceutical, Japan), followed by thorough mixing.

EXAMPLE 7

A glass vial (capacity:ca. 5 ml) containing 1 ml of Hirtonin Injection (Takeda Chemical, Japan) containing 1.464 mg of thyrotropin releasing hormone (TRH) tartrate and 50 mg of D-sorbitol was added 1 ml of 1% chondroitin sulfate preparation (Kaken Pharmaceutical, Japan), followed by thorough mixing.

EXAMPLE 8

In 1.5 ml of physiological saline for injection was dissolved 450 micrograms of parathyroid hormone (PTH) (Bachem Fine Chemicals, Switzerland). A glass vial containing 1 ml of the above solution was added 1 ml of 1% chondroitin sulfate preparation (Kaken Pharmaceutical, Japan), followed by thorough mixing.

EXAMPLE 9

In 1.5 ml of 1/30M phosphate buffer (pH 6) was added 750 micrograms of leuprorelin acetate (Takeda Chemical, Japan. U.S. Pat. No. 4,008,209), a LH-RH analogue. A glass vial containing 1 ml of the above solution was added 1 ml of 1% chondroitin sulfate preparation (Kaken Pharmaceutical, Japan), followed by thorough mixing.

EXAMPLE 10

In 0.5 ml of physiological saline was added 1 ml of interleukin 2 (corresponding to 10 micrograms) solution (produced by the method described in Japanese Patent Application Laid-open No. 78799/1986 corresponding to EP-176,299 and purified by the method described in Japanese Patent Application Laid-open No. 115528/1985 corresponding to EP-145,390; mixture of N-terminal Met-containing species and N-terminal Met-free species). A glass vial containing 1 ml of the above solution was added 1 ml of 1% chondroitin sulfate preparation (Kaken Pharmaceutical, Japan), followed by thorough mixing.

EXAMPLE 11

To a solution containing 100 ATU (about 8 μg) of hirudin (Peninsula Laboratories Inc., U.S.A.) was added physiological saline for injection to make the whole volume of 1 ml. A glass vial containing the above solution was added 1 ml of 1% chondroitin sulfate preparation (Kaken Pharmaceutical), followed by thorough mixing.

EXAMPLE 12

To 0.7 ml of physiological saline containing 20 μg of Serratia-derived superoxide dismutase (SOD) (Japanese Patent Application Laid-open No. 29285/1982 and No. 16685/1983 corresponding to EP-45,222 and EP-70,656, respectively) was added 1 milliliter of 1% chondroitin sulfate preparation (Kaken Pharmaceutical), followed by thorough mixing.

EXPERIMENTAL EXAMPLE 1

The following two injections were further prepared and subjected to testing.

Comparative Preparation 1: Physiological saline for injection (2 ml) was added to each vial of a human erythropoietin preparation (Epogin Injection 3000; Chugai Pharmaceutical) containing 3,000 international units of human erythropoietin, 25 mg of mannitol and 1 mg of human serum albumin to cause dissolution of the preparation.

Comparative Preparation 2: Physiological saline for injection 2 ml.

The injections of Examples 1 and 2 and Comparative Preparations 1 and 2 were respectively administered subcutaneously to 8-week-old male SD rats on their back at a dose for 7 days corresponding to 135 international units/kg/day twice at an interval of one week. Before administration and at regular intervals after administration, about 0.4-milliliter portions of blood were taken (EDTA 2Na used as an anticoagulant). The blood samples were respectively drawn into microhematocrit capillary tubes (Doramont Scientific, U.S.A.) and hematocrit values were determined (model KH120M centrifuge, Kubota Corporation, Japan).

Figure 1:
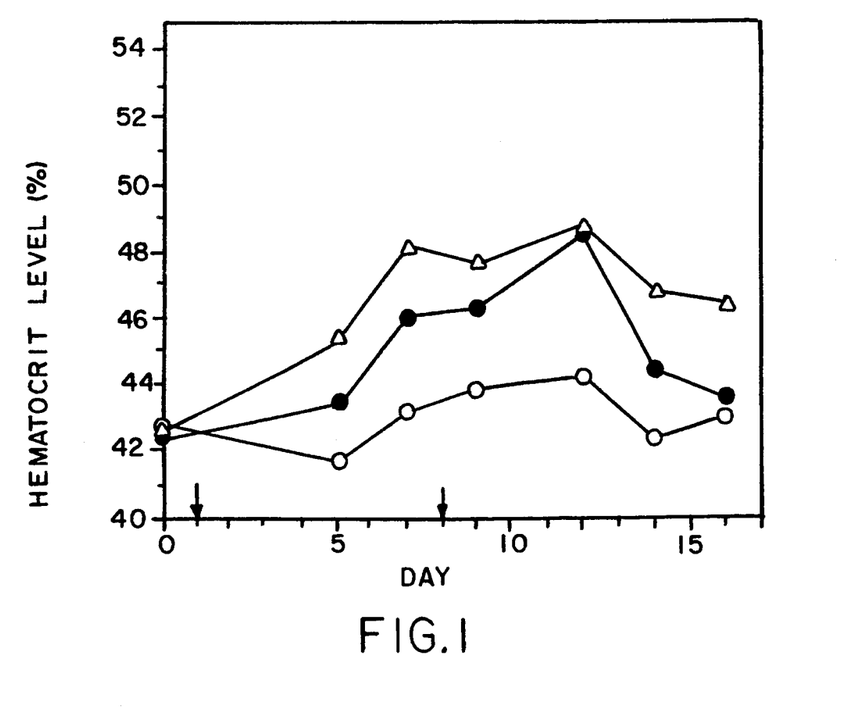
FIG. 1 graphically shows the time courses of hematocrit value, as observed in Experimental Example 1.

The results obtained with the preparation of Example 1, Comparative Preparation 1 and Comparative Preparation 2 are shown in FIG. 1. The figure shows the time courses of change in hematocrit value as found in the groups of rats injected twice, at a one-week interval, with the long-acting erythropoietin preparation of Example 1 (Δ), Comparative Preparation 1 (simple erythropoietin injection) ( ) and Comparative Preparation 2 (physiological saline) (o), respectively. As is apparent from FIG. 1, almost no changes were observed in hematocrit value in the group given Comparative Preparation 2, i.e. physiological saline. In the other two groups, the hematocrit values rose after the first administration and showed a fall on the 7th day after said administration, but yet the hematocrit value in the group given the preparation of Example 1 was higher than in the group given Comparative Preparation 1. After the second administration, the hematocrit value in the group given the preparation of Example 1 was maintained at an increased level till day 14 while the hematocrit value in the group given Comparative Preparation 1 rose rapidly and they fell again. This means that the addition of chondroitin sulfate to erythropoietin makes it possible to obtain a prolonged pharmacological effect while suppressing an abrupt change in pharmacological effect.

Figure 2:
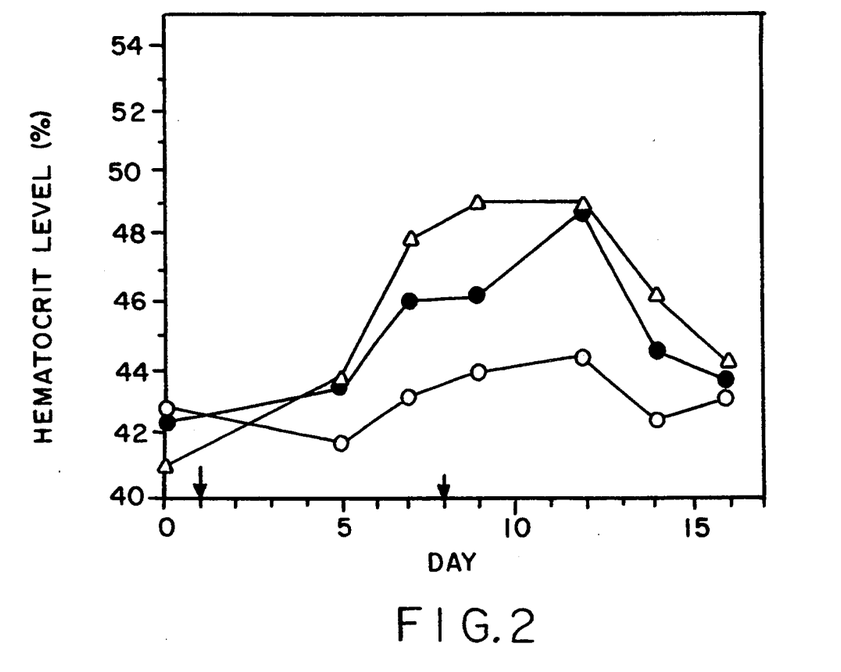
FIG. 2 graphically shows the time courses of hematocrit value, as observed in Experimental Example 1.

The results obtained with the preparation of Example 2, Comparative Preparation 1 and Comparative Preparation 2 are shown in FIG. 2. The figure shows the time courses of hematocrit value as found in the groups of rats injected twice, at a one-week interval, with the long-acting erythropoietin preparation of Example 2 (Δ), Comparative Preparation 1 (simple erythropoietin injection ( ) and Comparative Preparation 2 (physiological saline) (o), respectively. Rats were used in groups of five. Each mark in the figure shows a mean value. As is seen in FIG. 2, the hematocrit value rose after the first administration in the group given the preparation of Example 2, though somewhat later than in the group given Example 1. In the former group, an increased hematocrit value lasted over a certain period before and after the second administration. It is evident that the addition of chondroitin leads to a prolonged manifestation of the pharmacological effect of erythropoietin.

EXPERIMENTAL EXAMPLE 2

The following two injections were further prepared and subjected to testing.

Comparative Preparation 3: Physiological saline for injection (2 ml) was added to each vial of a human erythropoietin preparation (Epogin Injection 3000; Chugai Pharmaceutical) containing 3,000 international units of human erythropoietin, 25 mg of mannitol and 1 mg of human serum albumin to cause dissolution of the preparation.

Comparative Preparation 4: Physiological saline for injection 2 ml.

The injection of Example 3, Comparative Preparation 3 and Comparative Preparation 4 were respectively administered subcutaneously to 8-week-old male SD rats on their back at a dose for 7 days corresponding to 135 international units/kg/day twice at an interval of one week. Before administration and at regular intervals after administration, about 0.4-milliliter portions of blood were taken (EDTA 2Na used as an anticoagulant). The blood samples were respectively drawn into microhematocrit capillary tubes (Dramont Scientific) and hematocrit values were determined (model KH120M centrifuge, Kubota Corporation, Japan).

Figure 3:
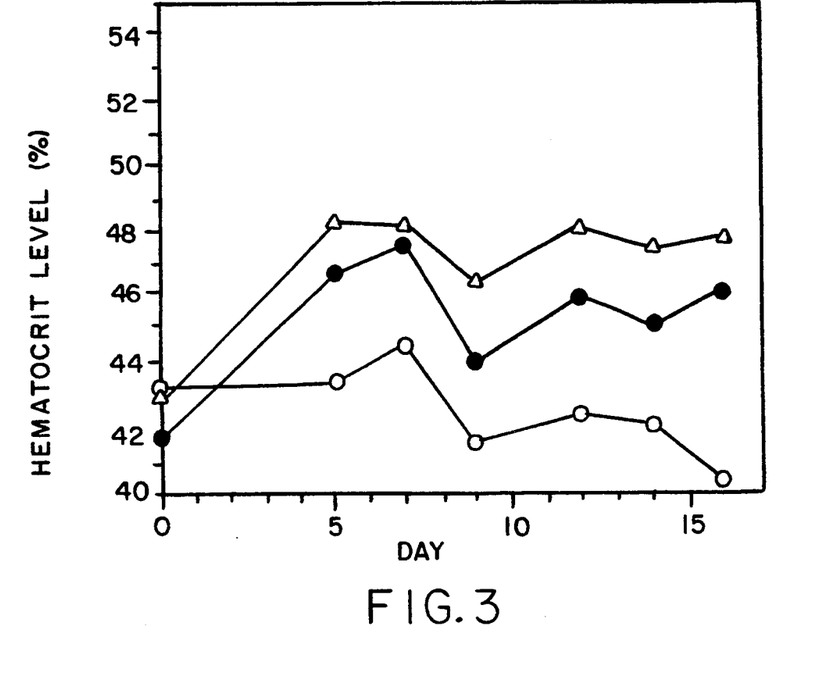
FIG. 3 graphically shows the time courses of hematocrit value, as observed in Experimental Example 2.

The results are shown in FIG. 3. The figure shows the time courses of hematocrit value as found in the groups of rats given Comparative Preparation 4 (physiological saline) (o), Comparative Preparation 3 (simple erythropoietin solution) ( ) and the erythropoietin- and heparan sulfate-containing solution of Example 3 (Δ), respectively, twice at an interval of 1 week. As is clear from FIG. 3, the hematocrit value in the group given Comparative Preparation 4, i.e. physiological saline, changed but showed no tendency toward increase. In the group given the preparation of Example 3 containing heparan sulfate and erythropoietin, the hematocrit value increased rapidly after the first administration and showed an almost constant, increased level over a period before and after the second administration until day 14. On the contrary, the hematocrit value in the group given Comparative Preparation 3 (simple erythropoietin solution) rose gradually after the first administration, reached a maximum on day 7 and then showed a great fall on day 9On day 12 of experiment, the hematocrit value showed an increase again as a result of the second administration. These results demonstrate that the addition of heparan sulfate to erythropoietin makes it possible to obtain a prolonged manifestation of the pharmacological effect while suppressing an abrupt change in pharmacological effect.

EXPERIMENTAL EXAMPLE 3

The following injection was further prepared and tested.

Comparative Preparation 5: Distilled water for injection (1 ml) was added to each vial of an interferon alfa preparation (Canferon A300; TAKEDA Chemical, Japan) containing 3 million international units of interferon alfa-2a and 5 mg of human serum albumin to cause dissolution of the preparation. To 1.2 ml of the resultant solution was added 0.6 ml of physiological saline for injection (Fuso Pharmaceutical), followed by thorough mixing.

Eight-week-old male SD rats were subcutaneously dosed by injection at their back, with the interferon alfa-2a containing preparation of Example 4 or Comparative Preparation 5 in volume of 0.3 milliliter. Before administration and serially after administration, about 0.4 ml portions of blood were collected. The serum was separated from each blood sample and assayed for serum interferon alfa-2a level by ELISA.

Figure 4:
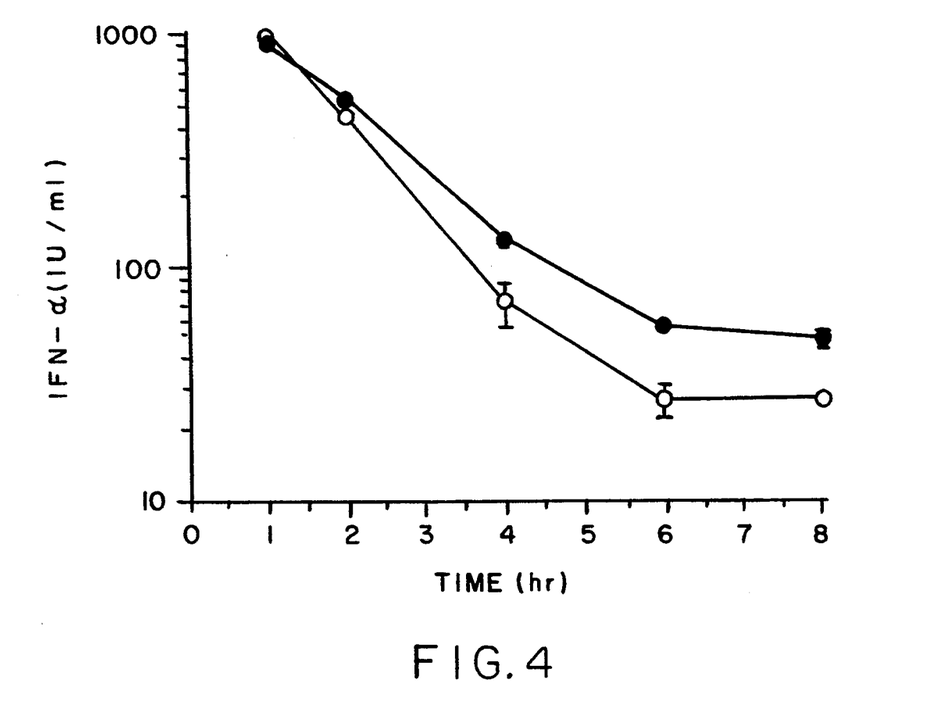
FIG. 4 graphically shows the time courses of serum interferon alfa level, as observed in Experimental Example 3.

The results are plotted in FIG. 4. Interferon alfa-2a was rapidly absorbed from the injection site in the control group treated with Comparative Preparation 5 and the serum interferon alfa-2a concentration fell with time (o). On the other hand, in the group treated with the preparation of Example 4 containing chondroitin sulfate, human serum albumin, and interferon alfa-2a, the serum interferon alfa-2a concentrations were higher compared with those of the control group from 2 hours till 8 hours after administration ( ). These results manifest the positive effect of the combination of chondroitin sulfate, human serum albumin, and interferon alfa-2a in sustaining the serum drug concentrations. Each point represents the mean of five rats.

EXPERIMENTAL EXAMPLE 4

The following composition was further prepared and tested.

Comparative Preparation 6: To 0.02 ml of granulocyte colony stimulating factor (G-CSF) preparation (Nupogen; Amgen, U.S.A.) containing 300 micrograms of G-CSF, 50 milligrams of mannitol, and 0.004% of Tween 80 was added 1.805 ml of physiological saline for injection (Fuso Pharmaceutical, Japan), followed by thorough mixing.

Eight-week-old male SD rats were subcutaneously dosed by injection at their back, with the human G-CSF-containing preparation of Example 5, or Comparative Preparation 6 in a volume of 0.3 milliliter. Before administration and serially after administration, about 0.1 milliliter of blood was withdrawn (EDTA-2Na used as anticoagulant). Peripheral leukocytes, erythrocytes and platelets were counted using a CC-180A microcell counter (Toa Iyo Denshi, Japan). Peripheral neutrophil, lymphocyte, monocyte and eosinophil counts were estimated by multiplying the respective cell occurrence frequencies, as found by typing, under a microscope, of 200 leukocytes for each Giemsa-stained smear preparation, by the leukocyte count.

Figure 5:
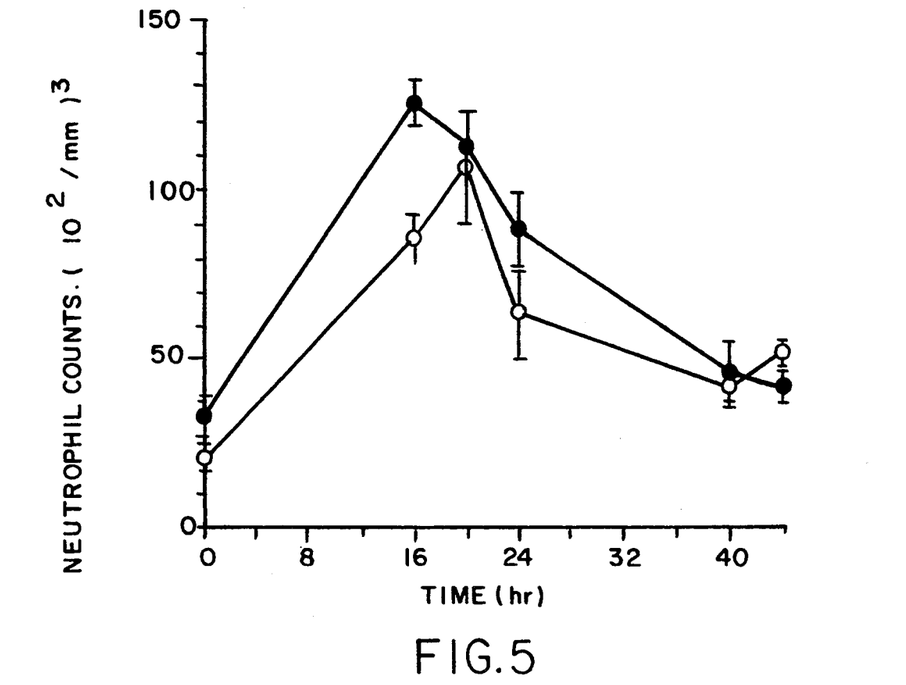
FIG. 5 graphically shows the time courses of absolute neutrophil counts in peripheral blood, as observed in Experimental Example 4.

The results thus obtained are shown in FIG. 5. In the positive control group (o) given the human G-CSF solution (Comparative Preparation 6), the peripheral blood 16 hours after administration showed an increased neutrophil count. In the group ( ) given the preparation of Example 5, which contained human G-CSF in combination with chondroitin sulfate, the peripheral blood showed a still further increase in neutrophil count.

At 24 hours after administration, the peripheral blood neutrophil counts in the group given Example 5 was still higher than the positive control group given Comparative Preparation 6. These results demonstrate that the addition of chondroitin sulfate can potentiate the pharmacological effect of G-CSF. In the figure, each point indicates a mean of 5 rats.

EXPERIMENTAL EXAMPLE 5

The following composition was further prepared and tested.

Comparative Preparation 7: In 5 ml of 0.1N hydrochloric acid was added 10 mg of pig insulin (Diosynth; Netherland). A glass vial (capacity: ca. 5 ml) containing 1 ml of the above solution was added 1 ml of physiological saline for injection, followed by thorough mixing.

Eight-week-old male SD rats were subcutaneously dosed by injection at their back, with the insulin containing preparation of Example 6 or Comparative Preparation 7 in a volume of 0.2 ml. Before administration and serially after administration, about 0.4 ml of blood was withdrawn for the determination of serum glucose level (Glucose C Test Wako, Wako Pure Chemical, Japan).

Figure 6:
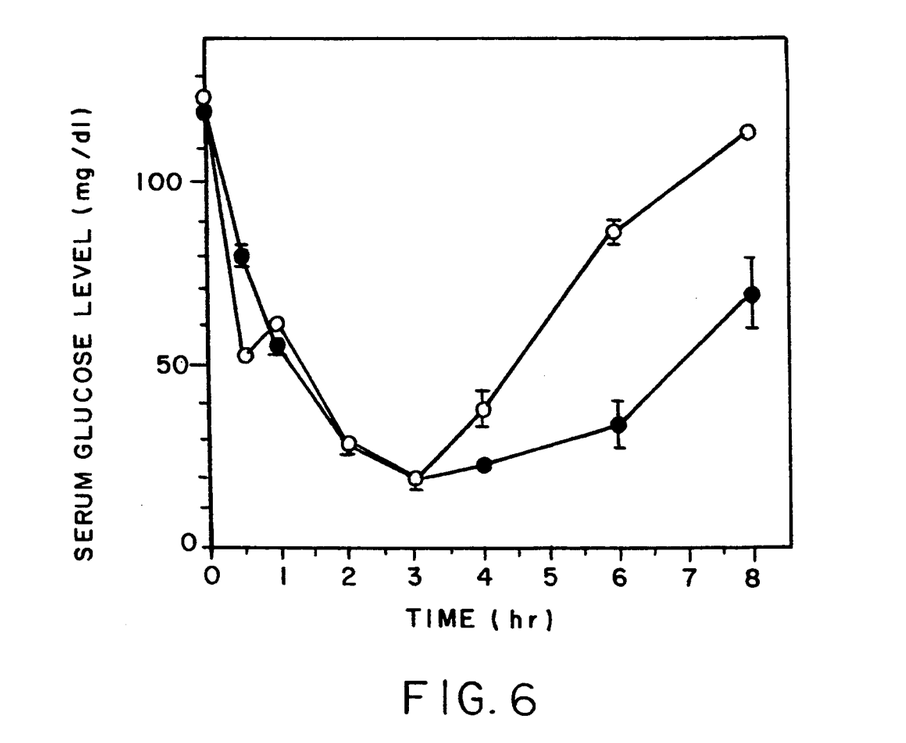
FIG. 6 shows the time courses of serum glucose levels, as observed in Experimental Example 5.

In FIG. 6, the time courses of serum glucose level are shown. There was no difference in the serum glucose levels between the group given the insulin composition of Example 6 ( ) and the group given the composition of Comparative Preparation 7 (o) till 3 hours post administration. Although the serum glucose level of the latter group returned to the pre-administration level at 8 hours post injection, the serum glucose level of the former group was adequately suppressed even at 8 hours post injection.

These results demonstrate that the positive effect of the combination of insulin and chondroitin sulfate in prolonging the pharmacological effect of insulin.

The following references, which are referred to for their disclosures at various points in this application, are incorporated herein by reference.

Japanese Patent Application Laid-open No. 121273/1975
Japanese Patent Application Laid-open No. 116465/1977
U.S. Pat. No. 3,959,247
U.S. Patent No. 4,100,152
Endocrinology, 129, 324 (1991)
The EMBO Journal, 11, 1867 (1992)
U.S. Pat. No. 4,008,209
Methods in Carbohydrate Chemistry, 5, 109 ff., 1965
Japanese Patent Application Laid-open No. 78799/1986
EP-176,299
Japanese Patent Application Laid-open No. 115528/1985
EP-145,390
Japanese Patent Application Laid-open No. 29285/1982
EP-45,222
Japanese Patent Application Laid-open No. 16685/1983
EP-70,656

What we claim is:

1. A water-soluble parenteral composition for injection which comprises (a) a water soluble pharmacologically active peptide selected from the group consisting of cytokines or hematopoietic factors, and (b) an alkali metal salt of a sulfate group-containing acidic mucopolysaccharide and/or a desulfated modification of a naturally occurring sulfate group-containing acidic mucopolysaccharide, wherein the weight ratio between (a) and (b) is about 0.001 to about 1:1, and wherein prior to injection, the tonicity and viscosity of the composition are adjusted by the addition of sterile water or sterile saline, to obtain a solution such that the viscosity of the solution is lower than 500 cP and the tonicity of the solution is from one-half to twice as high as that of physiological saline.

2. A water-soluble composition as claimed in claim 1, wherein the water-soluble pharmacologically active peptide is erythropoietin, granulocyte colony stimulating factor (G-CSF), macrophage colony stimulating factor (M-CSF), granulocyte-macrophage colony stimulating factor (GM-CSF), interferons or interleukins.

3. A water-soluble composition as claimed in claim 1, wherein the sulfate group containing acidic mucopolysaccharide and/or the desulfated modification of a naturally occurring sulfate group-containing acidic mucopolysaccharide is chondroitin sulfate, heparan sulfate, keratan sulfate, chondroitin or heparan.

4. A water soluble composition as claimed in claim 1, further comprising a water-soluble protein selected from the group consisting of serum albumin, globulin, collagen and gelatin, wherein the weight ratio between the water-soluble protein and the mucopolysaccharide is from about 0.0001:1 to 100:1.

5. A water soluble composition as claimed in claim 1, wherein the viscosity of said solution of the water soluble composition is lower than 400 cP.

* * * * *